(12) United States Patent
Park et al.

(10) Patent No.: US 6,746,842 B2
(45) Date of Patent: Jun. 8, 2004

(54) BIO-MOLECULAR CHIP AND MANUFACTURING PROCESS THEREOF

(75) Inventors: Han-Oh Park, Cheongwon-Kun (KR); Han-Il Ko, Cheongwon-Kun (KR)

(73) Assignee: Bioneer Corporation, Chungbuk (KR)

( * ) Notice: Subject to any disclaimer, the term of this patent is extended or adjusted under 35 U.S.C. 154(b) by 0 days.

(21) Appl. No.: 09/799,092

(22) Filed: Mar. 6, 2001

(65) Prior Publication Data

US 2002/0164592 A1 Nov. 7, 2002

(51) Int. Cl.$^7$ .......................... C12Q 1/68; G01N 33/53; A61K 38/00; C07H 21/02; C07H 21/04
(52) U.S. Cl. ........................ 435/6; 435/7.1; 435/287.2; 435/288.3; 530/300; 530/387.1; 536/23.1; 536/24.3
(58) Field of Search ................... 435/6, 7.1, 287.1, 435/287.2, 287.9, 288.3, 288.7; 530/300, 387.1; 536/23.1, 24.3

(56) References Cited

PUBLICATIONS

Karube, et al, 1977, Journal of Solid–Phase Biochemistry 2(1):41–44.*
Sambrook, J., ed. Molecular Cloning: A laboratory manual. Cold Spring Harbor Laboratory Press, 2nd Edition, 1989.*
Kiyohara, et al., 1996, Journal of Membrane Science 109:87–92.*
Smith, et al., 1985, Nucleic Acids Research 13(7):2399–2412.*
Kato et al. 1996 (Biotech. Bioeng. 51:581–590).*
Sundberg et al., "Derivatization Of Solid Supports And Methods For Oligomer Synthesis", U.S. 5,624,711, (Apr. 29, 1997).
Parinov et al., "DNA Sequencing By Hybridization To Microchip Octa– And Decanucleotides Extended By Stacked Pentanucleotides", *Nucleic Acids Research*, Oxford University Press, vol. 24(15):2998–3004, (1996).
Lamture et al., "Direct Detection Of Nucleic Acid Hybridization On The Surface Of A Charge Coupled Device", *Nucleic Acids Research*, Oxford University Press,, vol. 22(11):2121–2125, (1994).
Southern et al., "Analyzing And Comparing Mucleic Acid Sequences By Hybridization To Arrays Of 1017, Oligonucleotides: Evaluation Using Experimental Models", *Genomics*, Academic Press, Inc., vol. 13:1008– (1992)
Cantor et al., "Report On The Sequencing By Hybridization Workshop", *Genomics*, Academic Press, Inc., vol. 13:1378–1383, (1992).
Schena et al., "Quantitative Monitoring Of Gene Expression Patterns With A Complementary DNA Microarray", *Science*, vol. 270:467–470, (1995).

Maskos et al., "A Novel Method For The Analysis Of Multiple Sequence Variants By Hybridisation To Oligonucleotides", *Nucleic Acids Research*, Oxford University Press, vol. 21(9):2267–2268, (1993).
Williams et al., "Studies Of Oligonucleotide Interactions By Hybridisation To Arrays: The Influence Of Dangling Ends On Duplex Yield", *Nucleic Acids Research*, Oxford University Press, vol. 22(8):1365–1367, (1994).
Hacia et al., "Detection Of Heterozygous Mutations In BRCA1 Using High Density Oligonucleotide Arrays And Two–Colour Fluorescence Analysis", *Nature Genetics*, vol. 14:441–447, (1996).
Shoemaker et al, "Quantitative Phenotypic Analysis Of Yeast Deletion Mutants Using A Highly Parallel Molecular Bar–Coding Strategy", *Nature Genetics*, vol. 14:450–456, (1996).
Hoheisel, "Oligomer–Chip Technology", *Tibtech*, Elsevier Science Ltd., vol. 15:465–469, (1997).
Matson et al., "Biopolymer Synthesis On Polypropylene Supports: Oligonucleotide Arrays", *Analytical Biochemistry*, Academic Press, Inc., vol. 224:110–116, (1995).
Pease et al., "Light–Generated Oligonucleotide Arrays For Rapid DNA Sequence Analysis", *Proc. Natl. Acad. Sci. USA*, Biochemistry, vol. 91:5022–5026, (1994).
Sosnowski et al, "Rapid Determination Of Single Base Mismatch Mutations in DNA Hybrids By Direct Electric Field Control", *Proc. Natl. Acad. Sci. USA*, Biochemistry, vol. 94:1119–1123, (1997).
Saiki et al., "Genetic Analysis Of Amplified DNA With Immobilized Sequence–Specific Oligonucleotide Probes", *Proc. Natl. Acad. Sci. USA,*, Genetics, vol. 86:5230–6234, (1989).
Yershov et al., "DNA Analysis And Diagnostics On Oligonucleotide Microchips", *Proc. Natl. Acad. Sci. USA,*, Genetics,, vol. 93:4913–4918, (1996).
Vasiliskov et al., "Fabrication Of Microarray Of Gel–Immobilized Compounds On A Chip By Copolymerization", *BioTechniques*, vol. 27(3):592–605, (1999).
Strizhkov et al., "PCR Amplification On A Microarray Of Gel–Immobilized Oligonucleotides: Detection Of Bacterial Toxin– And Drug–Resistant Genes and Their Mutations", *BioTechniques*, vol. 29(4):844–857, (2000).

* cited by examiner

*Primary Examiner*—Ethan Whisenant
(74) *Attorney, Agent, or Firm*—Birch, Stewart, Kolasch & Birch, LLP (57) ABSTRACT

The present invention relates to a bio-molecular microchip and manufacturing process thereof. More particularly, the present invention is directed to a bio-molecular microchip comprising a substrate; and an amine group-containing bio-molecule immobilized onto a glycidyl moiety-containing polyacrylamide gel via covalent bonds formed between the glycidyl moiety of the polyacryl amide gel and the amine group of the bio-molecule by epoxy ring-opening reaction.

14 Claims, 5 Drawing Sheets

A-1. Quantitative analysis of
brightness spots along with row a

B-1. Quantitative analysis of the
brightness of spots along with
column 1

A-2. Quantitative analysis of
brightness of spots along with row b

B-2. Quantitative analysis of the
brightness of spots along with
column 2

BIO-MOLECULAR CHIP AND MANUFACTURING PROCESS THEREOF

TECHNICAL FIELD OF THE INVENTION

The present invention relates to a bio-molecular microchip and a manufacturing process thereof. More particularly, the present invention is directed to a bio-molecular microchip comprising a substrate, and an amine group-containing bio-molecule that is immobilized onto a glycidyl moiety-containing polyacrylamide gel via covalent bonds formed between the glycidyl moiety of the polyacryl amide gel and the amine group of the bio-molecule by epoxy ring-opening reaction; a manufacturing process thereof.

BACKGROUND OF THE INVENTION

As is known, oligonucleotide hybridization technique wherein oligonucleotide or target DNA fragment is immobilized on a gel or solid surface, is applied in the various fields. Recently, these oligonucleotide hybridization technique has been applied to DNA sequencing method, and various kinds of research relating to them have been made (Barinaga, M. (1991) Science 253:1489; Cantor, C. R., Mirzabekov, A. and Southern, E. (1992) Genomics 13, 1378–1383; Southern, E. M., Maskos, U. and Elder, J. K. (1992) Genomics 13, 1008–1017; Lipshutz, R. J., Morris, D., Chee, M., Hubbell, E., Kozal, M. J., Shai, N., Shen, N., Yang, R. and Fodor, S. P. A. (1995) Biotechniques 19: 442–447). Also, a number of methods for DNA immobilization on a gel or a solid surface have been developed. They are largely divided into two groups. One is to synthesize oligonucleotides directly on a glass surface, the other is to first synthesize oligonucleotides and immobilized this synthesized oligonucleotides on a solid surface or a gel surface.

For example, Southern et al. has disclosed a method for synthesizing oligonucleotides on a glass surface, comprising: a) immobilizing silicon rubber tubing on a glass surface by using of silicon rubber cement, b) overlapping the glass prepared in a) on a glass to be used in synthesizing oligonucleotides, c) injecting coupling solutions through the channel formed by overlapping to synthesize oligonucleotides in the specific site, and d) rotating sequentially silicon rubber tubing to synthesize oligonucleotides in the rest sites which is blocked(Southern, E. M., Maskos, U. and Elder, J. K. (1992) Genomics 13, 1008–1017; Maskos. U. and Southern, E. M. (1992) Nucleic Acids Res. 20, 1675–1678; Maskos, U. and Southern, E. M. (1993) Nucleic Acids Res. 21, 2267–2268; Williams, J. C., Case-Green, S. C., Mir, K. U. and Southern, E. M. (1994) Nucleic Acids Res. 22, 1365–1367).

Generally, oligonuclotides can be synthesized on a glass surface directly by using photosensitive oligonucleotide synthesis which is applied to DNA sequencing. In the above method, a free hydroxyl group is formed onto the surface which induced photosensitive protector from 5' hydroxyl group by light emitted through shield mask, and then deoxynucleosides which are protected after forming free hydroxyl group are linked on the surface(Pease, A. C., Solas, D., Sullivan, E. J., Cronin, M. T., Holmes, C. P. and Foder, S. P. A. (1994) Proc. Natl. Acad. Sci. USA 91, 5022–5026; Sapolsky, R. J. and Lipshutz, R. J. (1996) Genomics 33, 445–456; Hoheisel, J. D. (1997) Trends in Biotechnology 15, 465–469; Afftmetrix corp.).

The process for immobilizing oligonucleotides on polyacrylamide of which amide moiety is replaced with hydrazide group, has been developed by Russian scientists. In the above process, 3'-methyluridine at 3'-end of oligonucleotides is activated by sodium periodite($NaIO_4$) to form dialdehyde groups. Microchip for arranging oligonucleotides in the gel(100×100×20 $\mu$m) through the above method has been disclosed(Yershov, G., Barsky, V., Belgovskiy, A., Kirillov, E., Kreindlin, E., Ivanov, I., Parinov, S., Guschin, D., Drobishev, A., Dubiley, S., and Mirzabekov, A. (1996) Proc. Natl. Acad. Sci. U.S.A. 93, 4913–4918; Parinov, S., Barsky, V., Yershov, G., Kirillov, E., Timofeev, E., Belgovsky, A. and Mirzabekov, A. (1996) Nucleic Acids Res. 24, 2998–3004). Also, the method for immobilizing the oligonucleotides on the polypropylene film(PP-$NH_2$), which are aminized by phosphoramidite-based synthesizing process has been disclosed(Matson, R. S., Rampal, J., Pentoney, S. L., Jr., Anderson, P. D. and Coassin, P. (1995) Analytical Biochemistry 224, 110–116). Another method for arranging oligonucleotides is to immobilize 3'-amino altered oligonucleotides on a thin film of silicone dioxide($SiO_2$), which is formed on a surface of the silicone chip, during the nucleic acid hybridization. In this method, the 3'-amino altered oligonucleotide is fixed onto the thin film of silicone dioxide ($SiO_2$) through an epoxy ring-opening reaction of 3'-amino linkage with a epoxysilane monolayer, which is prepared by treating with 3'-glycidoxypropyltrimethoxysilane(Lamture, J. B., Beattie, K. L., Burke, B. E., Eiggers, M. C., Ehrlich, D. J., Fowler, R., Hollis, M. A. Kosicki, B. B., Reich, R. K., Smith, S. R., Varma, R. S. and Hogan, M. E. (1994) Nucleic Acids Res. 22, 2121–2125). Moreover, a method for inducing covalent bonds has been disclosed. In this method, the covalent bonds are induced by spotting oligonucleotides tailed with homopolymers(dTTP), to activate the thymine base of the oligonucleotide by Ultraniolet(UV) irradiation (Saiki, R. K., Walsh, P. S., Levenson, C. H. and Erlich, H. A. (1989) Proc. Natl. Acad. Sci. USA 86, 6230–6234). Further, a method improved from the above method has been disclosed. This method enables to make a more stable bond by forming amide bone between the amino-linker combined oligonucleotide and the carboxyl groups of the nylon membranes, and to increase efficiency of hybridization (Zhang, Y., Coyne, M. Y., Will, S. G., Levenson, C. H. and Kawasaki, E. S. (1991) Nucleic Acids Res. 19, 3929–3922). The hybridization techniques by adding a radioactive labeled or non-radioactive labeled target DNA to the DNA chip which is developed by methods described above, are successfully used to detect RAS point mutation, cystic fibrosis deletion, and other various point mutation detection as well as DNA sequencing (Cantor, C. R., Mirzabekov, A. and Southern, E. (1992) Genomics 13, 1378–1383; Zhang Y., Coyne, M. Y., Will, S. G. Levenson, C. H. and Kawasaki, E. S. (1991) Nucleic Acids Res. 19, 3929–3933; Hacia, J. J., Brody, L. C., Chee, M. S., Fodor, S. P. A. and Collins, F. S. (1996) Nature Genetics 14, 441–447; Shoemaker, D. D., Lashkari, D. A., Morris, D., Mittman, M. and Davis, R. W. (1996) Nature Genetics 14, 450–456; Sosnowski, R. G., Tu, E., Butler, W. F., O'Connel, J. P. and Heller, M. J. (1997) Proc. Natl. Acad. Sci. USA 94, 1119–1123). These methods can be very effective, especially in genetic mutation tests and genetic polymorphism research (Lipshutz, R. J., Morris, D., Chee, M., Hubbell, E., Kozal, M. J., Shai, N., Shen, N., Yang, R. and Fodor, S. P. A. (1995) Biotechniques 19, 442–447; Schena, M., Shalon, D., Davis, R. W. and Brown, P. O. (1995) Science 270, 467–470; Chee, M., Yang, R., Hubbell, E., Berno, A., Huang, X. C. Stern, D., Winkler, J., Lock, D. J., Morris, M. S. and Fodor, S. P. A. (1996) Science 274, 610–614; DeRisi, J., Penland, L. and Brown, P. O.; Bittner, M. L., Meltzer, P. S., Ray, M., Chen, Y., Su, Y. A. and Trent, J. M. (1996) Nature Genetics 14, 457–460). Also, it is predicted that the above methods can be used as ideal tools for diagnosis of infectious and genetic/hereditary diseases as well as mutant analysis such as neoplasm, HLA typing and the like in view of their sensitivity, unity and reproducibility. (Saiki. R. K., Walsh, P. S., Levenson, C. H. and Erlich, H. A. (1989) Proc. Natl. Acad. Sci. USA 86, 6230–6234; Zhang, Y., Coyne, M. Y., Will, S. G., Levenson, C. H. and Kawasaki, E. S. (1991) Nucleic Acids Res. 19, 3929–3933).

Methods for an oligonucleotide arrangement on a glass surface through direct photolithographic synthesis or other synthetic methods are very difficult requiring high-level techniques. One of the problems is that products on solid surface is relatively low, and thus requires further future consideration for adequate and appropriate quantitative analysis.

In contrast, a DNA chip by using a gel of the present invention allows direct arrangement of the oligonucleotides that is synthesized in conventional method, onto a surface, with a desired amount of concentration. A DNA fix capacity of polyacrylamide gel is 50 mM, and 1.5 $\mu$mol up to 1.5 mmol concentration can be used for oligonucleotide chip arrangement and hybridization procedure (Yershov, G., Barsky, V., Belgovskiy, A., Kirillov, E., Kreindlin, E., Ivanov, I., Parinov, S., Guschin, D., Drobishes, A., Dubiley, S., and Mirzabekov, A. (1996) Proc. Natl. Acad. Sci. U.S.A. 93, 4913–4918; Parinov, S., Barsky, V., Yershov, G., Kirillov, E., Timofeev, E., Belgovsky, A. and Mirzabekov, A. (1996) Nucleic Acids Res. 24, 2998–3004). It corresponds to 0. 5 to 50 fmol of oligonucleotide per a square 40×40×20 $\mu$m. It is 100 times higher than the second dimensional fix capacity of a glass surface (Yershov, G., Barsky, V., Belgovskiy, A., Kirillov, E., Kreindlin, E., Ivanov, I., Parinov, S., Guschin, D., Drobishev, A., Dubiley, S., and Mirzabekov, A.(1996) Proc. Natl. Acad. Sci. U.S.A. 93, 4913–4918). Therefore, The DNA chip produced using the gel of the present invention can be used in various fields and also can be manufactured conveniently.

SUMMARY OF THE INVENTION

The present invention is directed to a bio-molecular microchip comprising a substrate, and an amine group-containing bio-molecule, such as nucleotides, polypeptides or chemical compounds, which is immobilized onto a glycidyl moiety-containing polyacrylamide gel via covalent bonds formed between the glycidyl moiety of the polyacryl amide gel and the amine group of the bio-molecule by epoxy ring-opening reaction.

The reaction of an amine group of a bio-molecule such as a nucleotide, a polypeptide or a chemical compound, with a glycidyl group of a polyacrylamide gel of the present invention, forms a stable covalent bond that bind the bio-molecule onto said gel. A bio-molecular microchip of the present invention may be used for detecting DNA, PCR products or oligonucleotides through hybridization of nucleotides immobilized on the polyacrylamide gel, and also be used for determination of the sensitivity and specificity of the detection.

It is therefore the object of the present invention to provide a process for manufacturing a bio-molecular microchip which comprises immobilizing an amine group-containing bio-molecule onto a glycidyl moiety-containing polyacrylamide gel via covalent bonds formed by an epoxy ring-opening reaction between the glycidyl moiety of the polyacrylamide gel and the amine group of the bio-molecule.

Another object of the present invention is to provide bio-molecular microchips comprising a substrate, and an amine group-containing bio-molecule that is immobilized onto a glycidyl moiety-containing polyacrylamide gel via covalent bonds formed between the glycidyl moiety of the polyacryl amide gel and the amine group of the bio-molecule by epoxy ring-opening reaction.

A still further object of the present invention is to provide a method for detecting DNA fragments conveniently and efficiently by means of hybridization using a DNA or RNA probe.

BRIEF DESCRIPTION OF THE DRAWINGS

The above objects and other advantages of the present invention will become more apparent by describing in detail a preferred embodiment thereof with reference to the attached drawings, in which.

DETAILED DESCRIPTION OF THE INVENTION

Hereinafter, the present invention will be described in more detail. However, the present invention explained below is given only for the explanation of embodiment of the present invention and not intended to limit the scope of the present invention.

The object of the present is achieved by providing a process for manufacturing a bio-molecular microchip, which comprises:

immobilizing a bio-molecule or a chemical compound that contains an amine group on a glycidyl moiety-containing polyacrylamide gel that is placed on a substrate, wherein the amine group of the bio-molecule is covalently bound to the glycidyl moiety of the polyacrylamide gel via epoxy ring-opening reaction.

Bio-molecules useful in the present invention can be nucleotides, polypeptides or chemical compounds, which contain an amine group.

The polyacrylamide gel of the present invention can be formed by reaction between methacrylate group of glycidylmethacrylate and acryl group of acrylamide during polymerization reaction of polyacrylamide comprising N,N'-methylenebisacrylamide, with glycidylmethacrylate monomer. N,N,N',N-tetramethylenediamine and 10% amoniumpersulfate are quantitatively added in the polyacrylamide solution as catalysts for gelation reaction. The gel can be also formed by copolymerizing glycidylmethacrylate and acrylamide monomers optionally in the presence of N,N'-methylenebisacrylamide.

Bio-molecules such as oliogonucleotides which contain amine groups on the 5'-terminal thereof, are immobilized onto said gel through covalent bonds formed by the epoxy ring-opening reaction between glycidyl moiety of the gel and amine group of bio-molecule. In the gel formation, the ratio of acrylamide to the N,N'-methylenebisacrylamide is 90 to 99.1:0.1 to 10 (w/v), desirably 99:1 (w/v). This allows oligonucleotids to be immobilized on the gel easily by relatively increasing pore size of the gel, and allows that the DNA fragments immobilized on the gel can be hybridized more easily. The concentration of the polyacrylamide solution of the present invention is 6 to 10%, desirably 8%. The amount of glycidylmethacrylate added on the polyacrylamide solution is 1 to 5% (w/v). In order to detect the hybridized products, PCR is used to produce biotin or fluorescent-labeled single strand DNA. And also, at least 5 pmol/μl or complementary one of three oligonucleotide is detected by the sensitivity and specificity test through EtBr staining method which mainly stained double-helix by hybridizing non-labeled homologous oligonucleotide.

Therefore, when the bio-molecular microchip of the present invention is used, specific gene may be detected more efficiently than conventional PCR method. Also, the bio-molecular microchip of the present invention will be useful in DNA sequencing, genetic mutation, and polymorphism research.

Hereinafter, the present invention will be described in more detail with reference to the following examples. The examples are given for illustration of the invention and not intended to be limiting the present invention in any manner.

EXAMPLE 1

Synthesis of Oligonucleotides Which Contain Amine Group

Oligonucleotides which contain amine group($NH_2$) linker on 5'-terminal thereof, were prepared by using DNA synthesizer (Perceptive Biosystems Model No. 8909/8909 manufactured by Bioneer Corporation). The followings are the DNA sequences of the oligonucleotides, prepared in this Example,

IPRO2 : 5' -5CGGATAAATCCACTCTGGCTGC-3' (SEQ ID NO: 1)

IPRO3 : 5' -5GTTATCACGGATCACAATGACGGCACTTAT-3' (SEQ ID NO: 2)

FRA2-1 : 5' -5GAAGGTAGCGACTCGTATTAGTGAATACGA-3' (SEQ ID NO: 3)

FRA2-2 : 5' -5GGCTACCATCAGGTACGTCTAATACTTCAT-3' (SEQ ID NO: 4)

wherein, 5 represents amine group ($NH_2$).

EXAMPLE 2

Preparation of the Polyacrylamide Gel by Adding Glycidylmethacrylate

Acrylamide monomer which comprises 1 wt % of N,N'-methylenebisacrylamide was polymerized in water to make polyacrylamide solution of which solid content is 8% (w/v). Glycidylmethacrylate were added on polyacrylamide solutions to make five(5) kind of mixture solutions of which glycidylmethacrylate content are 1% (w/v), 2% (w/v), 3% (w/v), 4% (w/v) and 5% (w/v), respectively. Then, as gelation catalysts, 4 μl of N,N,N',N'-tetrametylethylendiamine and 10 μl of 10% ammoniumpersulfate, were added on 1 ml of each mixture solutions thus prepared to obtain polyacrylamide gel.

EXAMPLE 3

Gel Formation on Surface of Slide Glass

A surface of slide glass (76×26 mm) for microscope was treated with binding solution(the mixture of 5 μl of 3-(trimethoxysillyl)propyl methacrylate, 5 μl of acetic acid and 990 μl of ethyl alcohol) and was dried. The polyacrylamide gel prepared by the process of Example 1, was poured on the surface of slide glass thus treated. The slide glass thus treated with polyacrylamide gel, was covered with another slide glass of which surface had been treated with glass coat solution produced by Sigma Co., Ltd. And then, the fixation reaction was proceeded for more than 2 hours to form polyacrylamide gel layer of which thickness is less than 20 μl, and with which glycidylmethacrylate was reacted and thus glycidyl moiety is combined thereon.

EXAMPLE 4

Fluoresceinamine Immobilization and Confirmation Thereof

Figure 1:
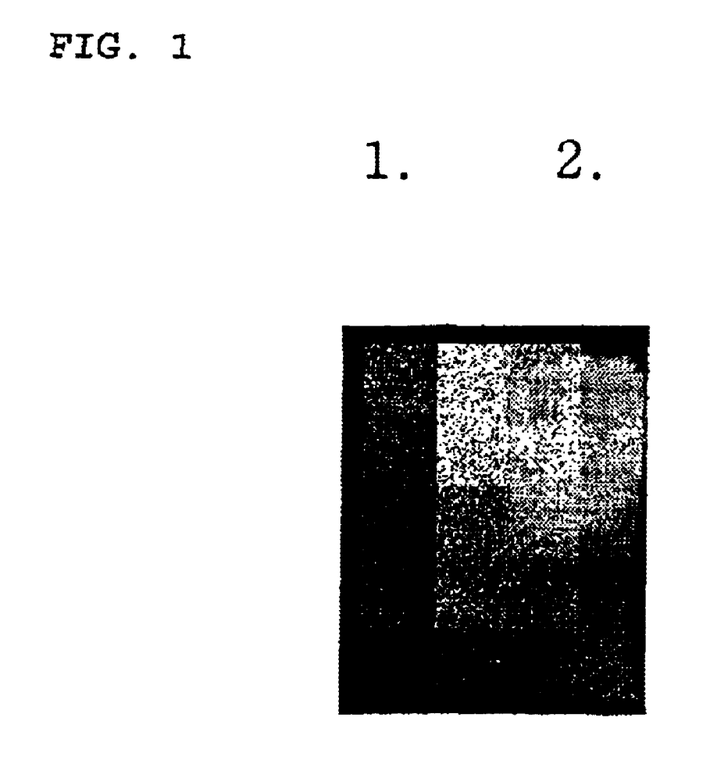
FIG. 1 is a photograph which represents fluoresceinamine immobilization on the polyacrylamide gel of the present invention.

To confirm the fixation reaction between amine and glycidyl moiety of the polyacrylamide gel layer, the mixture of 0.1M of sodium borate (pH9.5) and 0.5M fluoresceinamine(1:1), was spotted(the spot diameter was 5 mm) on the polyacrylamide gel which contains glycidyl moiety and on polyacrylamide gel which does not contain glycidyl moiety, and then fixation reaction were proceeded at room temperature for 30 minutes. Each spot was washed with water three times for 5 minutes per each time, and then, were examined by using the Ultraviolet(UV) transilluminator. As represented in FIG. 1, the fluorescence was detected only from the gel which contains glycidyl moiety and thereby, confirms that fluoresceinamine was bonded with the gel through the epoxy ring-opening reaction between glycidyl moiety and amine group. In the FIG. 1, lane 1 represents that the fluoresceinamine was not fixed on the gel which does not contains glycidyl moiety without glycidylmethacrylate,. The lane 2 represent that fluoresceinamine fixed in case of the fluoresceinamine fixation to the gel with 5% (w/v) glycidylmethacrylate,

EXAMPLE 5

Immobilization of Bio-molecule and the PCR Product on Polyacrylamide Gel

The said synthesized oligonucleotide which contains amine group or products of Polymerization Chain Reaction (Hereinafter, PCR products) which have the 295 or 129 DNA base pair originated from inv gene of the Yersinia genomic DNA were diluted in sodium borate (2.1M, pH9.3), and were spotted 3 times to the activated polyacrylamide gel in maximum diameter, 3 mm. Wherein, the PCR products were heat-treated at 100° C. for 5 minutes and immediately cooled in ice bath, and made into single strand DNA, then spotted. A immobilization reaction of oligonucleotide which contains amine group or PCR products was performed at room temperature for 30 minutes, and then oligonucleotide or PCR products were washed with water. 1M ethanolamine as blocking solution was added and reacted for 30 minutes then washed with water for 5 minutes 3 times in order to prevent further epoxy ring opening reaction by amine group. The slide glass was completely dried, and stored in 4° C. for next step reaction. Additionally, FRA2-1, oligonucleotide which contains amine group was done serial dilution up to 0.5 fmol and said oligoncletide was immobilized on the gel to measure the detection sensitivity by the EtBr staining of the oligonucleotide. And two types of oligonucleotides which contain amine group, IPRO2 and FRA2-2, were immobilized on gel using negative control to check peculiarity of detection method using EtBr.

Example of the Probe Preparation by Polymerization Chain Reaction Using Polymerization Enzyme The said oligonucleotides and the PCR products immobilized on gel and hybridization test was performed. Complementary oligonucleotide or the product of PCR-amplification was used as probe. 20 µl of PCR PreMix (1U, DNA polymerase which has heat-stability; 250 uM, each dNTP; 50 mM, Tris-HCl, pH 8.3; 40 mM, KCl, 1.5 mM, MgCl2; stablizer; loading dye, which produced by Bioneer Corporation) was used in all Polymerization Chain Reaction. In order to prepare biotin-labeled single strand DNA fragment with the 295 base pair of Yersinia inv gene which contains the complementary base pair, non-symmetrical Polymerization Chain Reaction was performed by using the PreMix PCR Kit which 2 pmol of IPRO2 sense primer, 20 pmol of KINV4 anti-sense primer(5'-CGTGAAATTAACCGTCACACT-3') (SEQ ID NO: 5) and 1 µM of biotin-11-dUTP(Beringer Manheim) were added. Wherein, the 10 ng of Yersinia genomic DNA, as a template, was used. Similarly, the fluorescent-labeled single strand DNA probe was prepared. Non-symmetrical Polymerization Chain Reaction was performed by adding 2 pmol of IPRO3 sense primer, 20 pmol of KINV4 anti-sense primer and 3 nmole of Amersham FluoroGreen. (Fluorescein-11-dUTP), to prepare fluorescent-labeled single strand DNA fragment with 129 base pair. The 10 ng of Yersinia DNA, as a template, was used. All PCR were performed 30 times at 94° C./ for 30 seconds; at 57° C. for 60 seconds; at 72° C. for 1 minute and 30 seconds, and pre-denaturation and last-extension were each performed at 94° C. for 5 minutes and at 72° C. for 5 minutes.

EXAMPLE 6

Hybridization Test Using Biotin-labeled Single Strand DNA Probe (295 Base)

Figure 2:
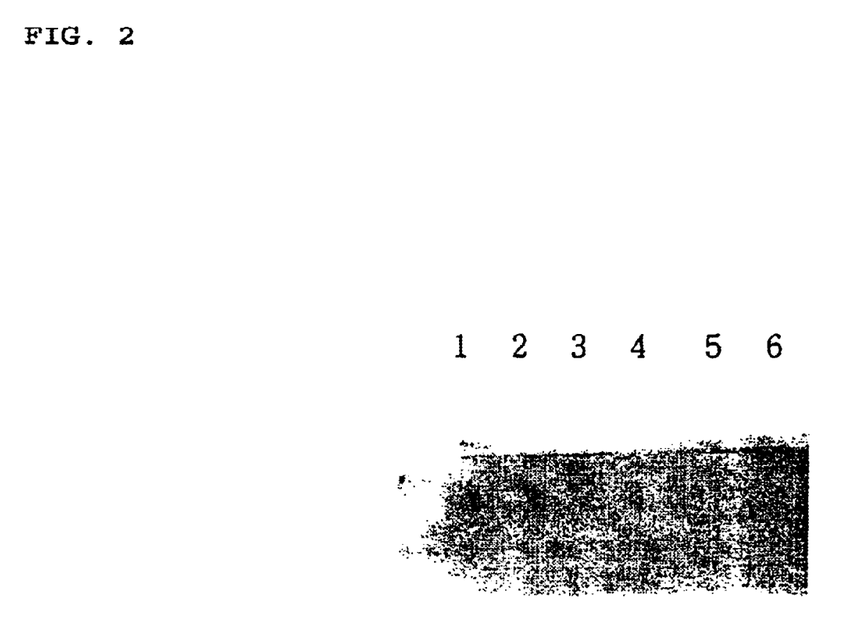
FIG. 2 is a photograph which represents the hybridization using biotin-labeled single strand DNA probe after the immobilization of PCR product and oligonucleotide(IPRO2) on the gel of the present invention.

20 µl of biotin-labeled single strand PCR solution prepared by non-symmetrical PCR was heat-treated at 95° C. for 5 minutes to be used as a probe(see to FIG. 2). 0.5 µl of single strand DNA with 295 base, 1 µl of PCR solution and the oligonucleotide(IPRO2) with 22 base of which final concentrations are 0.5 nmol and 1 nmol were immobilized on the gel, and then 5 ml of hybridization buffer solution (5×SSC, 1% blocking agent, 0.1% N-lauroylsacosin, 0.02% SDS) was added and pre-hybridized at 42° C. for 1 hour or more. Biotin-labeled single strand PCR solution was added therein and incubated at room temperature overnight. After hybridization, the slide glass was washed with 2×SSC and 0.1% SDS each for 5 minutes, with 0.1×SSC and 0.1% SDS each for 5 minutes, and with 1M maleic acid and 0.15M of NaCl solution each for 10 minutes. The slide glass was immersed for about 1 hour in alkaline phosphate buffer solution(150 mM of NaCl, 100 mM of Tris-HCl, pH 7.5) which Streptavidin-AP conjugate was added, and washed. And then the hybridized spot was detected by color reaction through adding NBT and BCIP. As illustrated in FIG. 2, when PCR products were spotted, the spot location was verifiable. however, in this case coloring sensitivity was weak and the spot has a tail like shape. On the other hand, when oligonucleotide was spotted, the coloring sensitivity was too weak to verify the spot location. In FIG. 2, lane 1 and lane 2 were 0.5 µl of single strand DNA with 295 base, lane 3 and lane 4 were 1 µl of single strand DNA with 295 base, lane 5 and lane 6 were 1 nmol and 0.5 nmol of IPRO2. Additionally, Since the coloring method using streptavidin-AP requires very long experimental steps and a lot of washing processes, it was not suitable for using in the bio-molecular chip of the present invention.

EXAMPLE 7

Hybridization Test Using the Fluorescent-labeled Single Strand DNA Probe(129 Base)

Figure 3:
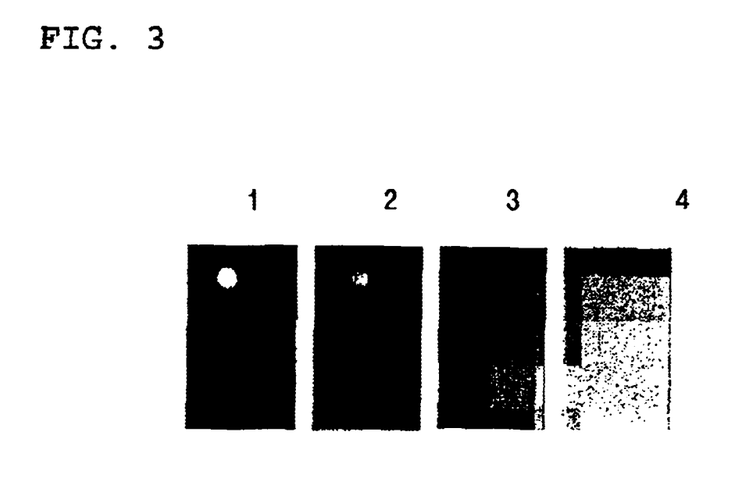
FIG. 3 is a photograph which represents the hybridization using fluorescent-labeled single strand DNA probe after the immobilization of oligonucleotide(IPRO3) on the gel of the present invention.

The fluorescent-labeled single strand DNA probe, 1 nmol of IPRO3 oligonucleotide was immobilized on slide glass, and 200 μl of 1× hybridization buffer solution which contains 20 μl of PCR solution made from probe was added on the slide glass and was reacted at room temperature for 30 minutes, and then washed 3 times for 5 minutes each times with hybridization buffer solution. The eplfluorescence microscope(excitation=490 nm,emission=520 nm) or UV transilluminator was used to test fluorescent reaction. The results thereof were represented in FIG. 3. In FIG. 3, lane 1 represents gel manufactured without using glycidylmethacrylate before washing, lane 2 represents gel manufactured without using glycidylmethacrylate before washing too, lane 3 represents gel manufactured without using glycidylmethacrylate after washing, and lane 4 represents gel manufactured with using glycidylmethacrylate after washing. As predicted, DNA was immobilized on the gel which contains glycidylmethacrylate, and even after washing, was also immobilized stably on the gel. Further, fluorescent-labeled single strand DNA probe test had higher fluorescent sensitivity and safety than biotin-labeled single strand DNA probe hybridization test and reduced the number of washing step.

EXAMPLE 8

Immobilization Ratio of Oligonucleotide Depending on Glycidyl Concentration

Figure 4:
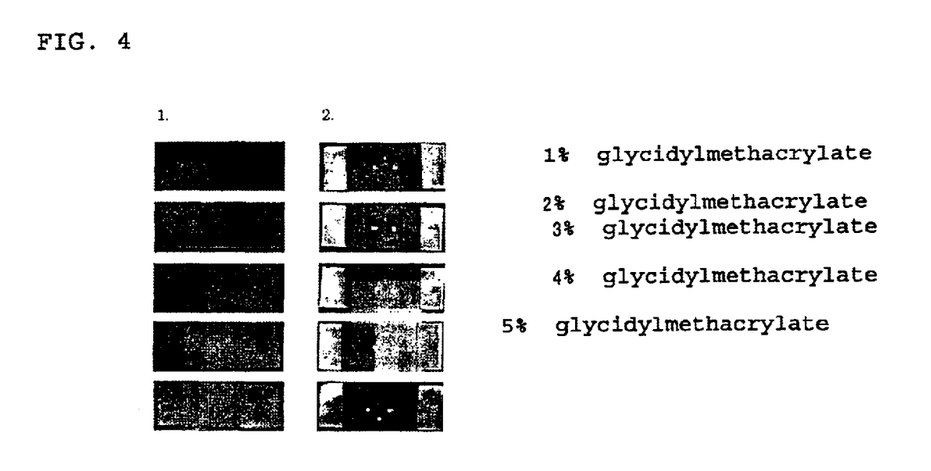
FIG. 4 is photographs which represent the immobilization ratio of oligonucleotides (FRA2-1) according to the glycidylmethacrylate concentration.

FRA2-1 oligonucleotide was immobilized on the gel made from 1% to 5% of various concentration of glycidylmethacrylate. The 1× hybridization buffer solution which comprises 10 pmol of complementary oligonucleotide, FRA2-1-2 (5'-TCGTATTCACTAATACGAGTC GCTACCTTC-3') (SEQ ID NO: 6), was poured on the gels. After the slide glass was set at room temperature for 30 minutes, was washed for 5 minutes with 1× hybridization buffer solution 3 times. And then 1 mM of EtBr solution in 0.1× hybridization buffer solution was prepared to be poured on the gel formed on the slide glass, and stained for 20 minutes, and subsequently washed with water several times. The hybridized oligonucleotide was, detected by UV transilluminator. As represented in FIG. 4, oligonucleotide was enabled to be immobilized even in 1% concentration of glycidylmethacrylate. By staining non-hybridized oligonucleotie, as control, with EtBr, hybridized DNA was compared with non-hybridized DNA. This comparison experiment was possible due to the characteristics of EtBr that couldn't inserted well into single strand DNA. In FIG. 4, lane 1 represents the oligonuclotide(FRA2-1) which was subsequently immobilized, non-hybridized and stained by EtBr, and lane 2 represents the oligonuclotide which was subsequently immobilized, hybridized with complementary oligonucleotide(FRA2-1-2) and stained by EtBr.

EXAMPLE 9

Figure 5:
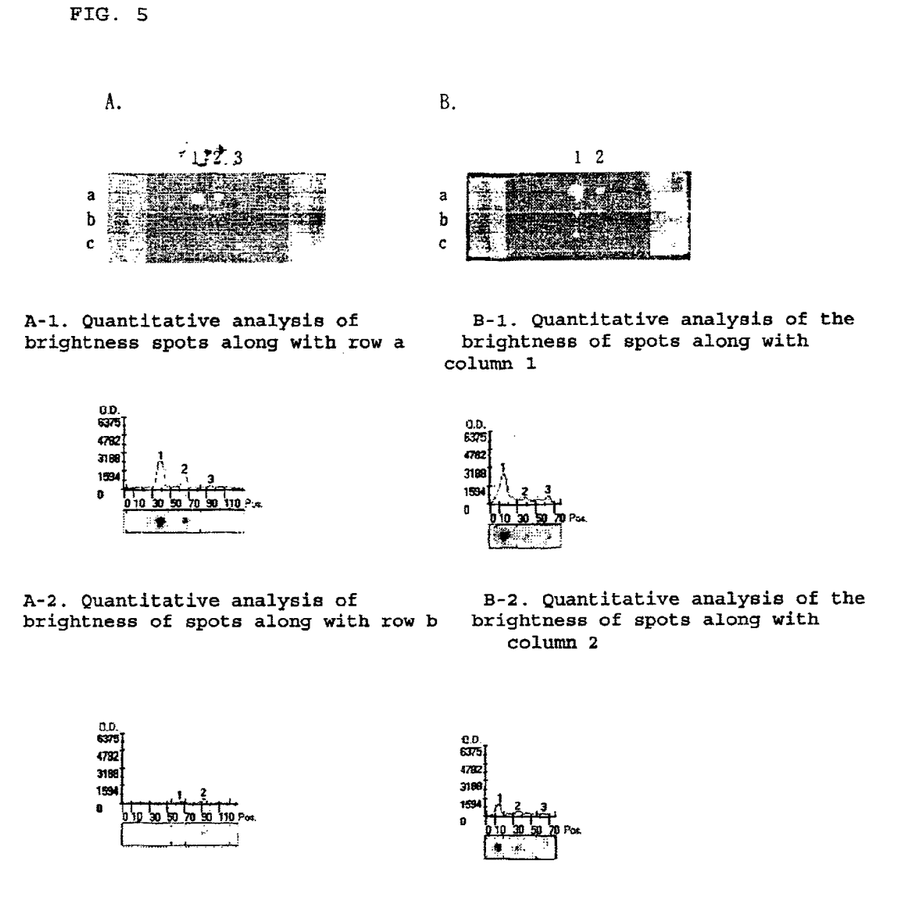
FIG. 5 is photographs and graphs which represent the sensitivity and specificity of the oligonucleotide hybridization by means of EtBr staining, and quantitative analysis thereof, respectively.

Hybridization Sensitivity and Hybridization Specificity of Oligonucleotide by EtBr Staining The test using the method used in above examples was performed to determine hybridization sensitivity and hybridization specificity of oligonucleotide. As illustrated in FIG. 5, 500 pmol/μl to 0.5 fmol/μl of oligonucleotides(FRA2-1) were arranged on the surface of the slide glass(see to FIG. 5-A), and 500 pmol/μl of non-complementary IPRO2 and 50 pmol/μl of non-complementary FRA2-2 were spotted on the surface, too(see to FIG. 5-B). FRA2-1 was hybridized with the complementary FRA2-1-2 oligonucleotide on the surface of the slide glass, and detected by EtBr staining. As a result, oligonucletide can be detected to the range of 5 pmol/μl and specifically hybridized DNA was detected to the range of 50 pmol/μl. Though the spot of the non-complementary oligonucleotide was enabled to detect, optical density(Hereinafter, OD) value by quantitative analysis of brightness, was remarkably low. In case of 500 pmol/μl of oligonucleotide, while the OD value of the complementary oligonucleotide was 2,645(FRA2-1), thoes of non-complementary oligonucleotide was 610(IPRO2) and 744 (FRA2-2). In case of 50 pmol/μl of oligonucleotide, the OD value of FRA2-1 was 1,148 and thoes of IPRO2 and FRA2-2 were 478 and 320, respectively(the image from Imager I was determined by 1D Main program; Bioneer Corporation). In FIG. 5, A and B represent the result of sensitivity and specificity, respectively. Particularly, a-1, a-2, a-3, b-1, b-2, b-3, c-1, c-2 and c-3 represent 500 pmol/μl of FRA2-1, 50 pmol/μl of FRA2-1, 5 pmol/μl of FRA2-1, 0.5 pmol/μl of FRA2-1, 500 fmol/μl of FRA2-1, 5 fmol/μl of FRA2-1, 0.5 fmol/μl of FRA2-1, 500 pmol/μl of FRA2-2 and 500 pmol/μl of IPRO2, respectively. Also, a-1, a-2, b-1, b-2, c-1 and c-2 represent 500 pmol/μl of FRA2-1, 50 pmol/μl of FRA2-1, 500 pmol/μl of IPRO2, 50 pmol/μl of IPRO2, 500 pmol/μl of FRA2-2, 50 pmol/μl of FRA2-2, respectively.

Industrial Applicability

As explained in detail above, the present invention relates to a bio-molecular microchip and process thereof. More particularly, the present invention is directed to a bio-molecular microchip which has a stable covalent bond between an amine group-containing bio-molecule, such as DNA, protein or antibody, and glycidyl group of a polyacrylamide gel by epoxy ring opening reaction of glycidylmethacrylate on the gel, and a manufacturing process thereof.

Moreover, complementary PCR products or specifically hybridized oligonucleotides can be detected and the sensitivity and specificity thereof can be determined by using of the bio-molecular microchip of the present invention.

Therefore, the bio-molecular microchip of the present invention, which can detect efficiently specific gene, is used in hybridization.

In conclusion, the present invention reduces the number of procedural step and the time required in comparison to the conventional hybridization methods. Additionally, bio-molecules such as amine group containing nucleotide, protein, and antibody can be immobilized on the gel by the process of the present invention, thus has wider field of applicability and use in DNA sequencing, genetic variation, and polymorphism research than the conventional DNA chip.

While the present invention has been particularly shown and described with reference to particular embodiment thereof, it will be understood by those skilled in the art that various changes in form and details may be effected therein without departing from the sprit and scope of the invention as defined by the appended claims.

What is claimed is:

1. A process for manufacturing a bio-molecular chip, comprising:

providing a substrate;

applying a layer of glycidyl moiety-containing polyacrylamide gel on said substrate; and then applying a bio-molecule that contains an amine group onto said layer, wherein said glycidyl moiety-containing polyacrylamide gel is formed by copolymerizing glycidylmethacrylate, and acrylamide or polyacrylamide, and wherein said bio-molecule is immobilized on said layer of polyacrylamide gel via a covalent bond between the amine group of the bio-molecule and the glycidyl moiety of the polyacrylamide gel via an epoxy ring-opening reaction.

2. A process according to claim 1, wherein said glycidyl moiety-containing polyacrylamide gel is formed by copolymerizing glycidylmethacrylate and acrylamide.

3. A process according to claim 1, wherein the glycidylmethacrylate is added into a solution of the polyacrylamide.

4. A process according to claim 3, wherein the polyacrylamide solution is prepared by using a gelation catalyst and polyacrylamide comprising 0.1 to 10 wt % of N,N'-methylenebisacrylamide.

5. A process according to claim 1, wherein said glycidylmethacrylate has a concentration of 1 to 5% (w/v).

6. A process according to claim 1, wherein 0.1 to 10 wt % of N,N'-methylenebisacrylamide is added.

7. A process according to claim 1, wherein the substrate is a glass plate.

8. A process according to claim 1, wherein the bio-molecule is selected from the group consisting of polynucleotides, oligonucleotides containing an amine group at 5' end, polypeptides and antibody.

9. A process according to claim 8, wherein the polynucleotides are DNA or RNA.

10. A bio-molecular chip comprising a substrate;

a layer of a glycidyl moiety-containing polyacrylamide gel; and a biomolecule, wherein said biomolecule is immobilized onto said layer of glycidyl moiety-containing polyacrylamide gel via a covalent bond formed between the glycidyl moiety of said polyacrylamine gel and the amine group of the bio-molecule by epoxy ring-opening reaction.

11. A method for using the bio-molecular microchip of claim 10, wherein said immobilized bio-molecule is a nucleic acid and a specific nucleic acid is detected through hybridization with a DNA or RNA probe.

12. The method of claim 11, wherein the probe is labeled with fluorescent material to detect a bio-molecule.

13. The method of claim 12, wherein said fluorescent material is inserted selectively between the double helix structure to detect a bio-molecule.

14. The method of claim 11, further comprising DNA sequencing, analysis of genetic variation, or polymorphism research.

* * * * *

SEQUENCE LISTING

<160> NUMBER OF SEQ ID NOS: 6

<210> SEQ ID NO 1
<211> LENGTH: 22
<212> TYPE: DNA
<213> ORGANISM: Artificial Sequence
<220> FEATURE:
<223> OTHER INFORMATION: Synthesized oligonucleotide IPRO2

<400> SEQUENCE: 1
cggataaatc cactctggct gc                                          22

<210> SEQ ID NO 2
<211> LENGTH: 30
<212> TYPE: DNA
<213> ORGANISM: Artificial Sequence
<220> FEATURE:
<223> OTHER INFORMATION: Synthesized oligonucleotide IPRO3

<400> SEQUENCE: 2
gttatcacgg atcacaatga cggcacttat                                  30

<210> SEQ ID NO 3
<211> LENGTH: 30
<212> TYPE: DNA
<213> ORGANISM: Artificial Sequence
<220> FEATURE:
<223> OTHER INFORMATION: Synthesized oligonucleotide FRA2-1

<400> SEQUENCE: 3
gaaggtagcg actcgtatta gtgaatacga                                  30

<210> SEQ ID NO 4
<211> LENGTH: 30
<212> TYPE: DNA
<213> ORGANISM: Artificial Sequence
<220> FEATURE:
<223> OTHER INFORMATION: Synthesized oligonucleotide FRA2-2

<400> SEQUENCE: 4
ggctaccatc aggtacgtct aatacttcat                                  30

<210> SEQ ID NO 5
<211> LENGTH: 21
<212> TYPE: DNA
<213> ORGANISM: Artificial Sequence
<220> FEATURE:
<223> OTHER INFORMATION: PCR anti-sense primer KINV4

<400> SEQUENCE: 5
cgtgaaatta accgtcacac t                                           21

<210> SEQ ID NO 6
<211> LENGTH: 30
<212> TYPE: DNA
<213> ORGANISM: Artificial Sequence
<220> FEATURE:
<223> OTHER INFORMATION: Complementary oligonucleotide FRA2-1-2

<400> SEQUENCE: 6
tcgtattcac taatacgagt cgctaccttc                                  30